United States Patent [19]

Bigner et al.

[11] Patent Number: 5,407,925
[45] Date of Patent: Apr. 18, 1995

[54] REGIONAL CHEMOTHERAPY WITHIN THE CENTRAL NERVOUS SYSTEM WITH 4-HYDROPEROXYCYCLOPHOSPHAMIDE

[75] Inventors: Darell D. Bigner, Chapel Hill; Henry S. Friedman, Durham, both of N.C.; O. Michael Colvin, Baltimore, Md.

[73] Assignees: The Johns Hopkins University, Baltimore, Md.; Duke University, Durham, N.C.

[21] Appl. No.: 788,609

[22] Filed: Nov. 6, 1991

Related U.S. Application Data

[63] Continuation of Ser. No. 328,921, Mar. 27, 1989, abandoned.

[51] Int. Cl.$^6$ .............................................. A61K 31/66
[52] U.S. Cl. ...................................................... 514/110
[58] Field of Search ........................................ 514/110

[56] References Cited

U.S. PATENT DOCUMENTS 3,808,297  4/1974  Takamizawa ........................ 260/936

OTHER PUBLICATIONS

Arndt et al., "Intrathecal Admimistration of 4-Hydroperoxycyclophosphamide in Rhesus Monkeys", Cancer Research (1987) vol. 47 pp. 5932-5934.
Alberts et al., "Tabular Summary of Pharmocokinetic Parameters Relevant to In Vitro Drug Assay," ed. by Salmon, Cloning of Human Tumor Stem Cells, pp. 351-359.
Arndt et al., "Cerebrospinal Fluid Penetration of Active Metabolites of Cyclophosphamide and Ifosfamide in Rhesus Monkeys," Can. Res. (1988), 48:2113-2115.
Boerrigter et al., "Local Administration of the Cytostatic Drug 4-Hydroperoxycyclophosphamide(4-HPCY) Facilities Cell-Mediated Immune reactions", (1984) Clin. Exp. Immunol., 58:161-166.
Boerrigter et al., "Intradermal Administration of 4-Hydroperoxycyclophosphamide during Contact Sensitization Potentiates Effector T-Cell Responsiveness in Draining Lymph Nodes," Immunopharmacology (1986), 11:13-20.
Boerrigter et al., "Potentiation of T-Cell Mediated Immunity by Local Chemotherapy," Agents and Actions, (1984), 15:77-79.
Carter et al., "The integration of Chemotherapy into a Combiend Modality Approach for Cancer Treatment," Cancer Treatment Review (1975), 2:193-214.
Chang, "Differential Sensitivity of Pancreatic Adenocarcinoma Cell Lines to Chemotherapeutic Agents in Culture," Cancer Treat. Rep., (1983), 67:355-359.
Frei, III et al., "Dose: A Critical Factor in Cancer Chemotherapy," Amer. J. Med. (1980), 69:585-594.
Friedman et al., "Experimental Chemotherapy of Human Medulloblastoma Cell Lines and Transplantable Xenografts with Bifunctional Alkylating Agents," Can. Res. (1988), 48:4189-4195.
Mirabelli et al., "A Murine Model to Evaluate the Ability of In Vitro Clonogenic Assays to Predict the Response to Tumors in Vivo," Cancer Res. (1988), 48:5447-5454.
Niell et al., "The Use of a Tumor Colony Assay in Predicting Chemotherapeutic Drug Response in Murine Bladder Cancer," Cancer (1983), 52:619-625.
DeFabritiis et al., "Elimination of Clonogenic Burkitt's Lymphoma Cells from Human. Bone Marrow Using 4–Hydroperoxycyclophosphamide in Combination with Monoclonal Antibodies and Complement," Blood (1985), 65:1064-1070.
Colvin et al., "Pharmacology of Cyclophosphamide (List continued on next page.)

Primary Examiner—Jerome D. Goldberg
Attorney, Agent, or Firm—Banner, Birch, McKie & Beckett

[57] ABSTRACT

A method of treating human tumors is provided in which tumors are regionally treated with a cytolytic, pre-activated, bifunctional alkylating agent, namely 4-hydroperoxycyclophosphamide. The treatment is effective against a variety of tumor types within the central nervous systems.

10 Claims, 5 Drawing Sheets

OTHER PUBLICATIONS and Metabolites," Cancer Treatment Reports (1981), 65(Supp. 3):89–95.

Kubota et al., "Antitumor Effect and Metabolic Activation of Cyclophosphamide and 4-HC in the Human Breast Carcinoma (MX-1)-Nude Mouse System," Gann (1983),74:437–444.

Fuchs et al., "Activity of Intrathecal 4-HC in a Nude Rat Model of Human Neoplastic Meningitis," Cancer Research (1990),50:1954–1959.

O'Connell, "Current Status of Chemotherapy for Advanced Pancreatic and Gastric Cancer," J. Clin. Oncology (1985), 3:1032–1039.

Selby et al., "A Critical Appraisal of the Human Tumor Stem-Cell Assay," New Eng. J. Med., (1983),308:129–134.

Schein, "The Role of Chemotherapy in the Management of Gastric and Pancreatic Carcinomas," Seminars in Oncology (1985), 12:49–60.

Scheper et al., "Immunotherapeutic Effects of Local Chemotherapy with an Active Metobolite of Cyclophosphamide," Meth. and Find Exptl. Clin Pharmacol. (1987), 9:611–615.

REGIONAL CHEMOTHERAPY WITHIN THE CENTRAL NERVOUS SYSTEM WITH 4-HYDROPEROXYCYCLOPHOSPHAMIDE

The U.S. government has a paid up license in this invention and the right in limited circumstances to require the patent owner to license others on reasonable terms as provided for by the terms of grants numbered CA11898, CA43722, CA44640, NS20023. NS00958, and T32-NS07304, awarded by the National Institutes of Health.

This application is a continuation of application Ser. No. 328,921, filed Mar. 27, 1989, now abandoned.

TECHNICAL FIELD OF THE INVENTION

This invention relates to the use of chemotherapeutic agents. More particularly the invention relates to the use of 4-hydroperoxycyclophosphamide in regional chemotherapy within the central nervous system.

BACKGROUND OF THE INVENTION

Cyclophosphamide, an alkylating agent with a broad spectrum of anti-tumor activity is actually a prodrug which, to be activated must be converted by hepatic microsomal enzymes into 4-hydrocyclophosphamide. This compound subsequently undergoes spontaneous decomposition to a variety of biologically active compounds. Because of its requirement for hepatic activation, cyclophosphamide cannot be used for regional therapy.

In contrast, 4-hydroperoxycyclophosphamide (4-HC), a preactivated derivative of cyclophosphamide, exhibits equal toxicity on a molar basis to cells in vitro as 4-hydrocyclophosphamide, the principal cytotoxic metabolite of cyclophosphamide. (Redwood, et al., preceding of the American Association of Cancer Research, Vol. 23, p. 169, 1982.) 4-HC has been shown to be active in vitro against murine leukemia cells (Hilton, Bio. Chem. Pharmacol. Vol. 33, pp. 1867–1872, 1984), human breast cancer cells (Kubota, et al., GANN, Vol. 74, pp. 437–444, 1983). and Burkitt's lymphoma (De Fabritiis, et al., Blood, Vol. 65, pp. 1064–1070, 1985) cell lines. It is active against human cancer cell line MOLT-4 (a T-cell leukemia) at 2.5 uM, a rhabdomyosarcoma cell line at 8 uM, a breast cancer cell line McF-7 at 9.5 uM and the medulloblastoma cell line TE-671 at 12.8 uM (Arndt et al., Cancer Research, Vol. 47, p. 5932, 1985; Friedman et al., Cancer Research, Vol. 46, p. 2827, 1986.) 4-HC is currently used clinically to purge tumor cells from bone marrow prior to autologous marrow transplantation (Korbling, et al., British Journal of Hematology, Vol. 52, pp. 89–96, 1982; and Kizer, et al., Blood, Vol. 65, pp. 1504–1510, 1985).

In addition, it has been shown that direct intrathecal administration of 4-HC can achieve drug concentrations of 100 uM in the cerebrospinal fluid (which would be cytocidal in vitro) without producing toxicity. (Arndt et al., Cancer Research, Vol. 47, pp. 5932–5934, 1987).

Despite these preliminary findings, it has yet to be established whether 4-HC can effectively treat tumors in vivo. There is a distinct need in the art of tumor therapy for agents which can affect the growth of compartmentalized tumors. Such tumors are often aggressive and difficult to treat even after surgery and irradiation.

SUMMARY OF THE INVENTION

It is an object of the invention to provide a method of treating tumors which can grow and metastasize within the central nervous system.

In accordance with this invention, a method of treating a tumor in the human body is provided which comprises administering an effective amount of 4-hydroperoxycyclophosphamide directly to a tumor within the central nervous system, said tumor being sensitive to the cytotoxic effects of 4-hydroperoxycyclophosphamide.

The method of the present invention provides the art with a successful means of treating neoplasms for which current therapies are highly unsuccessful. The treatment of the present invention results in a delay in the onset of tumor related symptoms as well as in an increase in the survival of tumor-bearing individuals.

DETAILED DESCRIPTION OF THE INVENTION

Figure 1:
FIG. 1 shows histological analysis of leptomeningeal tumor extension from the cauda equina to the base of the brain.

It is a finding of the present invention that direct administration of 4-hydroperoxycyclophosphamide to the central nervous system containing a tumor can have a positive effect on both the survival time and the onset of tumor-related symptoms. A very broad spectrum of human tumors can be treated by the method of the present invention. Particularly preferred tumors for treatment in the present mode are those that commonly metastasize to the brain. These include carcinomas of the lung, breast, stomach, as well as melanomas. Tumors which invade the central nervous system can be treated by the method of the present invention.

Direct regional therapy can be accomplished according to the invention because of the preactivation of the drug. That is, unlike cyclophosphamide, the drug need not be processed by the liver before activity is available to the tumor site. In one preferred embodiment, the 4-HC is administered directly to the subarachnoid space of the brain.

A broad spectrum of human tumors can be effectively treated by the method of the present invention. These include but are not limited to medulloblastoma, glioma, carcinoma, rhabdomyosarcoma, breast cancer, sarcoma, melanoma, leukemia, and lymphoma. Medulloblastomas, the most common primary central nervous system malignancy in childhood, is a highly aggressive neoplasm with a marked predilection for leptomeningeal dissemination. Although therapeutic intervention for such dissemination in this tumor is often unsuccessful, the method of the present invention has proved successful in both delaying the onset of associated symptoms as well as increasing the median survival of the individuals affected.

In accordance with the present invention, administration of 4-hydroperoxycyclophosphamide can be by any means which causes a localized, regional effect. For example, the drug may be administered intrathecally or intraventricularly, directly into a tumor mass, or directly in the arterial blood supply to a tumor. These and other techniques, which are termed herein "direct administration to a region of the body," are well known in the medical arts.

After systemic administration of cyclophosphamide, concentrations of 4-hydroxycyclophosphamide of up to 20 uM are achieved. Direct regional administration of 4-hydroperoxycyclophosphamide can achieve much higher concentrations. Effective doses of 4-hydroperoxycyclophosphamide are generally those which create a regional concentration of between about 150 uM and about 2000 uM. Preferred doses are above about 200 uM; and most preferred are above about 500 uM. Doses between about 1000 uM and about 2000 uM can be employed. As is readily apparent to those of skill in the art, maximum concentrations are desirable for their cytocidal effects on the tumor cells; however these should not cause toxic side effects to other portions of the treated individual.

Precise doses and regimens can be empirically determined by those of skill in the art depending upon the particular condition of the patient and the tumor involved. Generally weekly administration of 4-HC is desirable, with monitoring for toxicity and efficacy. A course of about six weekly injections can be employed. To monitor toxicity neurological damage is measured and observed. For example, functional neurological loss, numbness, paralysis, or pain may be observed and should be minimized. 4-HC may be administered alone or in combination with other chemotherapeutic agents, such as methotrexate.

The following examples are not intended to limit the scope of the invention which has been described above.

EXAMPLE 1

This example describes the animal model which was used to test the efficacy of the method of the present invention in vivo in whole animals.

Female athymic nude rats (200–250 grams), maintained in the Duke University Animal Laboratory and Isolation Facility, were anesthetized with ketamine/xylazine (55 mg/ml ketamine, 9 mg/ml xylazine), administered i.p. at a volume of 1 ml/kg. Subarachnoid catheters were placed using a modification of the technique described by Kooistra, et al. (Cancer Research, vol. 46, pp. 317–323, 1986). Briefly, rats were placed with the neck flexed 90 degrees in a stereotactic frame with tilt adaptor (David Kopf Instruments, Tujunga, Calif.). A midline sagittal incision was made from the inion to the laminal arch of C1. The atlanto-occipital membrane was exposed by sharp dissection. The tough, outer membrane and underlying cisterna magna dura were opened using the tip of a 20-guage needle as a knife, under 5–10× magnification using an operating microscope (Zeiss OPMI 99). A PE-10 catheter (Intramedic, Clay Adams) with a 5-0 stainless steel wire styler was inserted into the subarachnoid space and passed along the posterior aspect of the spinal cord to the lumbar region (8.5 cm). A loose knot was tied in the catheter and fixed with dental epoxy (Lang Dental Manufacturing Co., Chicago, Ill.). The catheter was passed through the skin lateral to the incision using a 19-gauge needle. The wound was closed in three layers using 6-0 Ethicon (Ethicon Co., Somerville, N.J.). After documenting spontaneous flow of CSF, the catheter was concluded using a short length of 2-0 stainless steel wire. The animals were allowed to recover for three to five days and only animals showing normal motor and sensory function were used in experiments (greater than 99% of animals undergoing catheter placement). Injections of tumor cells or drugs were performed through the catheter in volumes of 20–40 ul using a Hamilton syringe and injector equipped with a 30 gauge needle. All injections were followed by 20 ul of sterile saline to rinse the cathether.

The establishment, characterization and tissue culture techniques for the human medulloblastoma cell line TE-671 have been previously described (McCallister et al., Int. J. Cancer, Vol. 20, pp. 206–212, 1977; and Friedman et al., J. Neurapathol. Exp. Neurol., Vol. 42, pp. 485–513, 1983). Cells were harvested in log phase into phosphate buffered saline (PBS) at $6.2 \times 10^6$ or $1.25 \times 10^7$ viable cells/ml, (as assessed by trypan blue exclusion) and $5 \times 10^5$ cells injected into subarachnoid catheters within 1 hour of harvest. Preliminary studies were performed to determine the optimum volume of tumor injection. Groups of 5 animals each were injected with $5 \times 10^5$ cells in either 20 ul or 40 ul.

EXAMPLE 2

This example shows the effect of tumor inoculation volume on the nude rats.

The effect of altering the volume of inoculated tumor cells was assessed using a constant dose of $5 \times 10^5$ TE-671 cells. At a 20 ul inoculation volume, animals developed progressive neurologic deficits and died at day 14–18. With a 40 ul injection volume, animals died by day 21–27, with leptomeningeal tumor extending from the cauda equina to the base of the brain (FIG. 1). For all further studies a 40 ul injection volume was used.

Histologic analysis documented leptomeningeal tumor extension from the cauda equina to the low cervical cord. The entire spine and skull were removed en bloc and fixed in 10% formalin for 7–10 days, then decalcified using RDO solution (Apex Engineering Products Co., Plainfield, Ill.). The brain and spinal cord were cut into six sections. Coronal sections of the brain were taken at the level of the coronal suture and the pituitary gland. Axial sections of the spinal cord were taken from the cervical, thoracic, and lumbar cord, and the cauda equina. Sections were embedded in paraffin, and 6 um sections were stained with hematoxylin and eosin and examined by light microscopy.

EXAMPLE 3

This example shows the effects of tumor inoculation on the nude rats.

Rats were inoculated with tumor cells as described above in example 1. Animals were followed until death with daily weights and neurologic examinations, including the presence or absence of the stepping and placing reflex, and the ability to negotiate a 60 degree incline ramp. These functions have been reported to correlate with subarachnoid tumor growth in other systems, in contrast to sensory function tests (Kooistra et al., Cancer Research, Vol.. 96, pp. 317–323, 1986).

Figure 2:
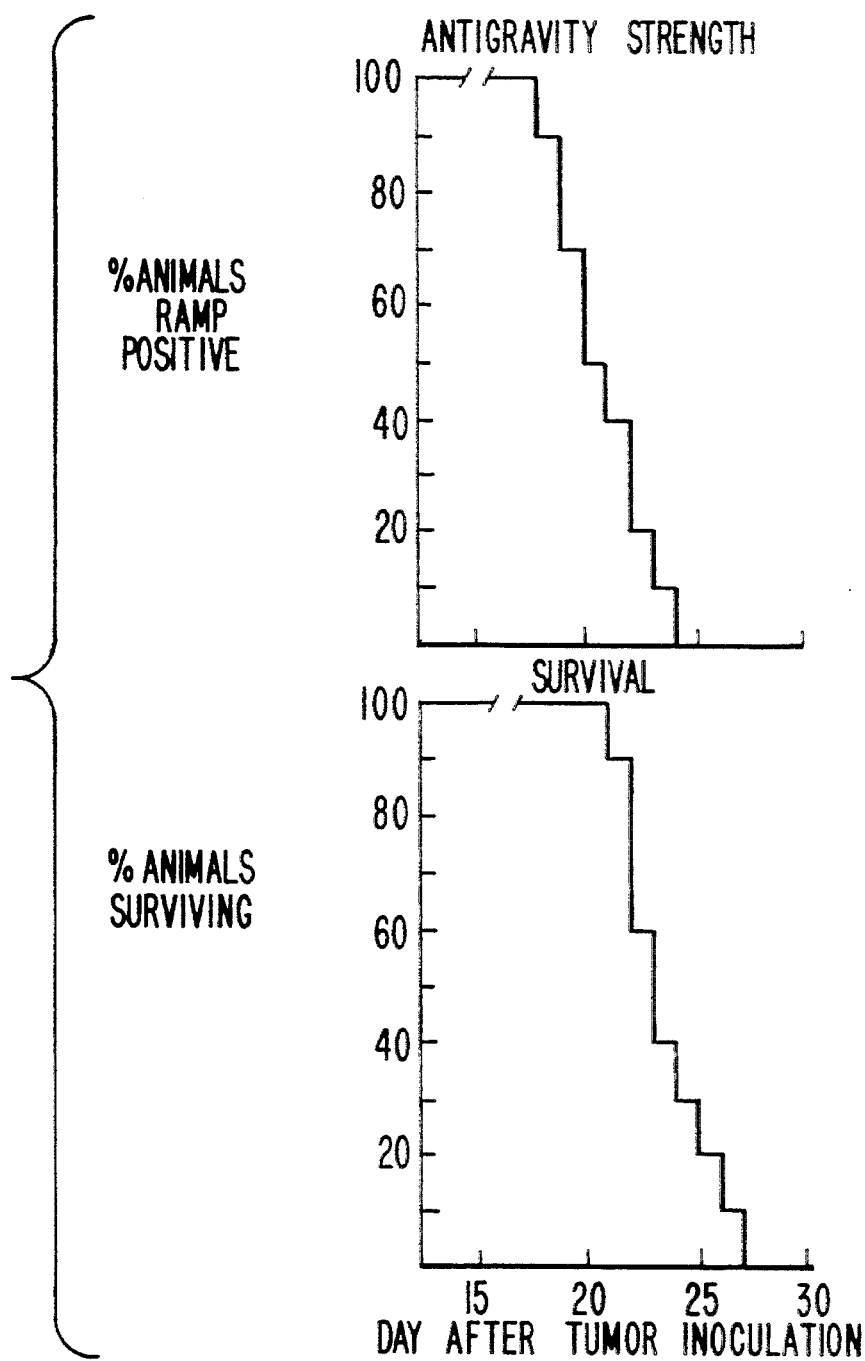
FIG. 2 shows the loss of anti-gravity strength and survival time of nude rats injected with TE-671 cells.

Animals injected with $5 \times 10^5$ TE-671 cells in 40 ul developed a progressive quadriparesis, with loss of ramp climbing ability and stepping and placing reflexes by day 18-24, with death generally occurring by day 21-27 (FIG. 2).

Figure 3:
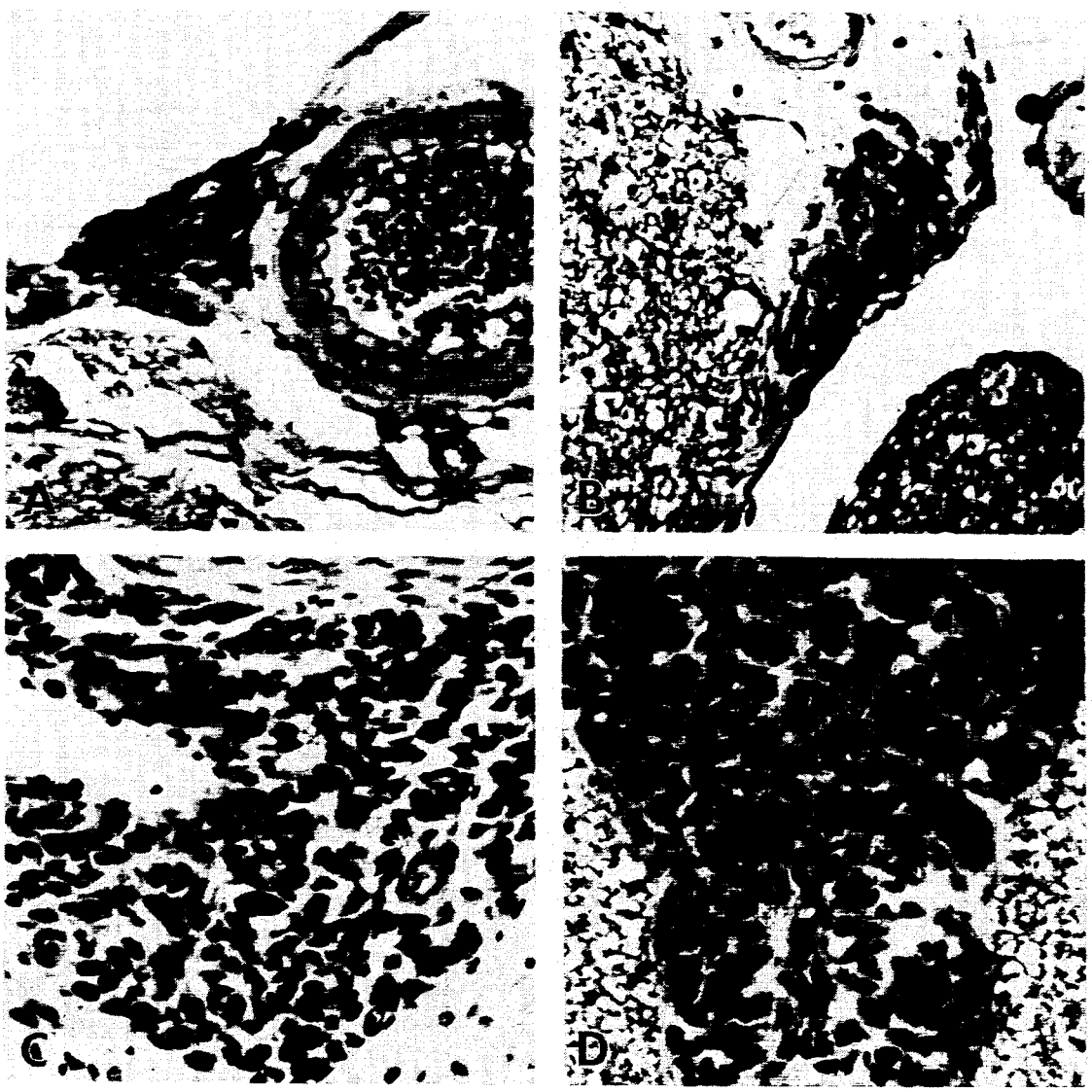
FIG. 3 shows histological sections from animals injected with TE-671 cells. On day eight (panels A and B) small focal nests of tumor cells were observed in the subarachnoid space. By day 20 (panels C and D) confluent filling of the subarachnoid space by tumor cells was observed.

On day 4, no tumor could be demonstrated. By day 8, sections from most animals showed focal small nests of tumor cells in the subarachnoid space (FIGS. 3A, B). By day 20, sections from most animals showed confluent filling of the subarachnoid space by tumor cells, which extended from the base of the brain to the cauda equina (FIG. 3C, D).

EXAMPLE 4

This example demonstrates the effects of regional administration of 4-HC on the loss of the antigravity response and on the survival rate caused by the tumor xenografts.

4-HC, was diluted in PBS and administered via subarachnoid catheter within one hour of its preparation on day 8 following tumor inoculation. In the first experiment, one group of 27 animals was treated with 40 ul 1 mM 4-HC to provide a final CSF concentration of 100 uM, based on the rat CSF volume of 400 ul (Meek and Neff, Neuropharmacology, Vol. 12, pp. 497–499, 1973). A control group of 10 animals received 40 ul PBS. Animals were followed as described above, with histopathology obtained on all animals after death. Statistical analysis was performed using the Wilcoxan rank sum test. A P of less than 0.05 was considered significant.

Figure 4:
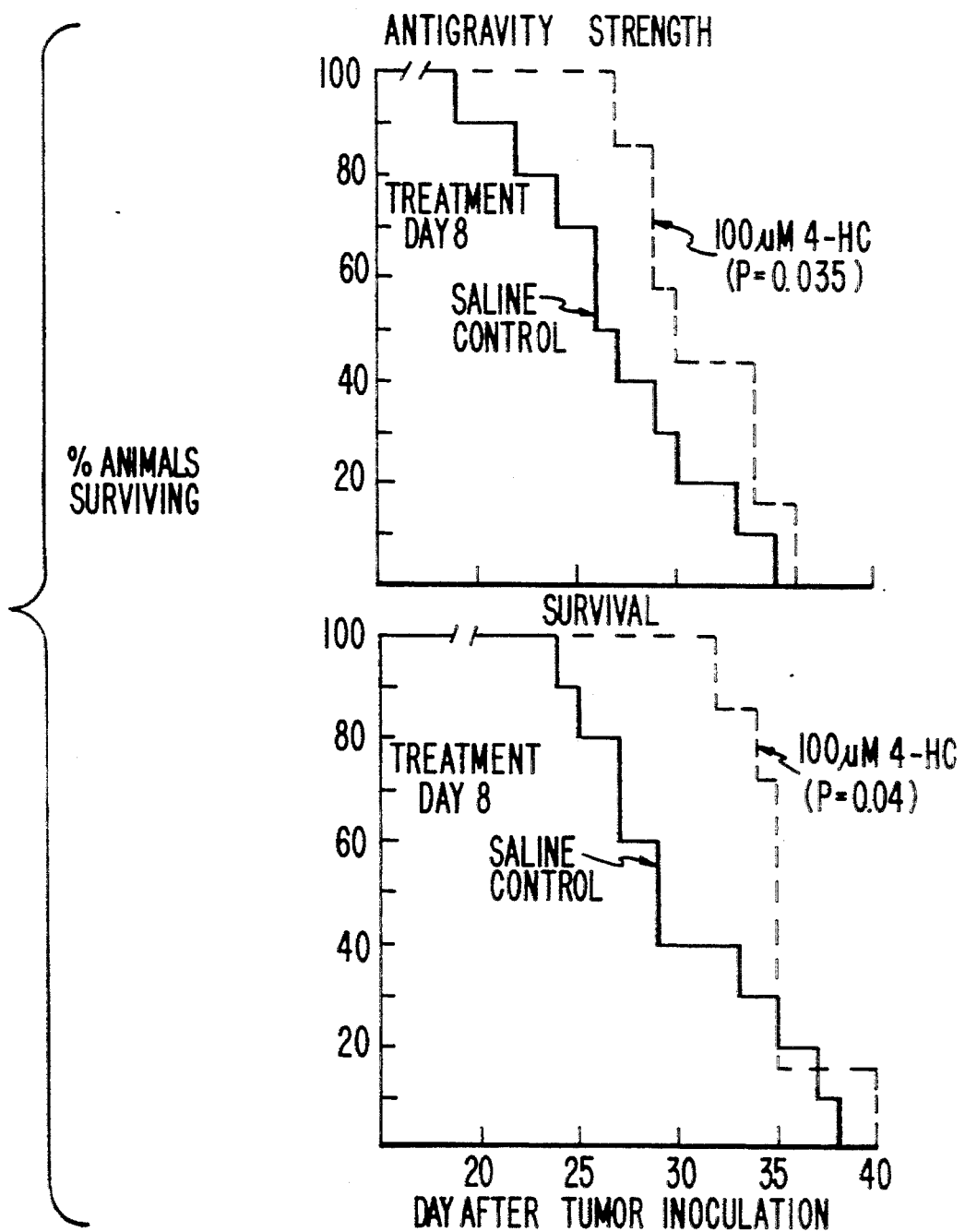
FIG. 4 shows the effect of intrathecal 4-HC treatment (to a final concentration of 100 uM) on both loss of anti-gravity strength and on survival time.
Figure 5:
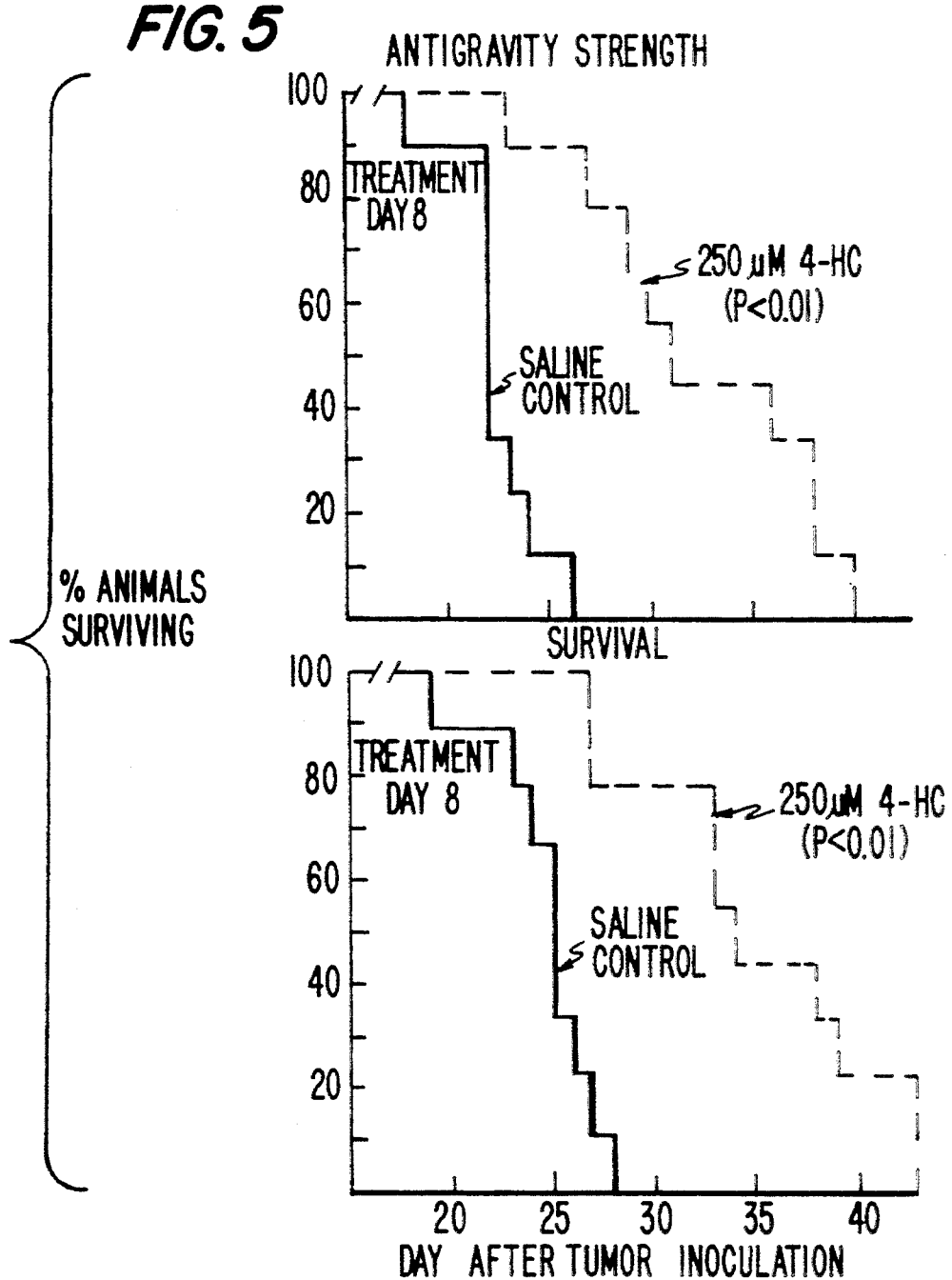
FIG. 5 shows the effect of an increased dose of 4-HC (to a final concentration of 250 uM) on both the loss of anti-gravity strength and on survival time.

Treatment with intrathecal 4-HC (final concentration 100 uM) resulted in a delay in the loss of antigravity strength (p=0.036) and an increase in median survival of 20% (p=0.04) (FIG. 4). Increase in the dose of 4-HC (to a final concentration of 250 uM) resulted in a further delay in the loss of antigravity strength (p less than 0.01) and an increase in median survival of 36% (p less than 0.01) (FIG. 5). There was no clinical evidence of toxicity with either dose. In both treatment studies, loss of stepping and placing reflexes and ramp climbing ability preceded death by approximately 3 days. Sections from all animals in both the 4-HC-treated and saline-treated control groups showed a diffuse subarachnoid infiltrate of tumor cells extending from the base of the brain to the cauda equina.

We claim:

1. A method of treating a tumor in the human body, comprising:
    administering an effective amount of 4-hydroperoxycyclophosphamide directly to a tumor within the central nervous system, said tumor being sensitive to the cytotoxic affects of 4-hydroperoxycyclophosphamide.

2. The method of claim 1 wherein the tumor has metastasized to the brain.

3. The method of claim 2 wherein the tumor is a medulloblastoma.

4. The method of claim 2 wherein the tumor is a carcinoma selected from the group consisting of lung, breast and stomach carcinomas or is a melanoma.

5. The method of claim 1 wherein the 4-hydroperoxycyclophosphamide is administered intrathecally.

6. The method of claim 1 wherein the 4-hydroperoxycyclophosphamide is administered to the subarachnoid space.

7. The method of claim 1 wherein the 4-hydroperoxycyclophosphamide is administered intraventricularly.

8. The method of claim 1 wherein the effective amount of 4-hydroperoxycyclophosphamide creates a concentration within the central nervous system of between about 150 and about 2000 $\mu M$.

9. The method of claim 8 wherein the effective amount of 4-hydroperoxycyclophosphamide creates a concentration within the central nervous system of between about 1000 $\mu M$ and about 2000 $\mu M$.

10. The method of claim 8 wherein the regional concentration is between about 500 uM and 1000 uM.

* * * * *